(12) United States Patent
Bayer et al.

(10) Patent No.: US 7,855,027 B2
(45) Date of Patent: Dec. 21, 2010

(54) METHODS AND APPARATUS FOR BREATH ALCOHOL TESTING

(75) Inventors: David J. Bayer, Richmond Heights, MO (US); M. Rankine Forrester, St. Louis, MO (US)

(73) Assignees: Intoximeters, Inc., St. Louis, MO (US); Alcotek, Inc., St. Louis, MO (US)

( * ) Notice: Subject to any disclaimer, the term of this patent is extended or adjusted under 35 U.S.C. 154(b) by 1014 days.

(21) Appl. No.: 10/572,253

(22) PCT Filed: Sep. 17, 2004

(86) PCT No.: PCT/US2004/030793

§ 371 (c)(1),
(2), (4) Date: Jan. 11, 2007

(87) PCT Pub. No.: WO2005/029619

PCT Pub. Date: Mar. 31, 2005

(65) Prior Publication Data

US 2007/0154765 A1 Jul. 5, 2007

Related U.S. Application Data

(60) Provisional application No. 60/504,448, filed on Sep. 19, 2003.

(51) Int. Cl.
*H01M 8/24* (2006.01)
*G01N 1/22* (2006.01)

(52) U.S. Cl. .......... 429/455; 429/466; 73/23.3
(58) Field of Classification Search .......... 429/345, 429/35, 455, 466; 73/23, 23.3
See application file for complete search history.

(56) References Cited

U.S. PATENT DOCUMENTS

| 4,744,953 | A | 5/1988 | Wolf et al. |
| 4,749,553 | A * | 6/1988 | Lopez et al. .......... 422/84 |
| 5,048,321 | A | 9/1991 | Chow |
| 5,393,495 | A | 2/1995 | Forrester |
| 5,400,637 | A | 3/1995 | Forrester |
| 6,464,941 | B1 | 10/2002 | Diekmann |
| 2003/0176803 | A1 | 9/2003 | Gollar |
| 2004/0138823 | A1 | 7/2004 | Gollar |
| 2005/0251060 | A1 | 11/2005 | Gollar |

FOREIGN PATENT DOCUMENTS

WO    WO 93/05393    *   3/1993

* cited by examiner

*Primary Examiner*—Patrick Ryan
*Assistant Examiner*—Thomas H. Parsons
(74) *Attorney, Agent, or Firm*—Armstrong Teasdale LLP

(57) ABSTRACT

A fuel cell assembly includes a fuel cell, a fuel cell housing, and a diaphragm. The fuel cell housing includes an endwall and an inlet port extending through said endwall. The inlet port is for admitting a breath sample into the housing. The diaphragm is coupled within the housing such that a cavity is defined between the housing and the diaphragm. The fuel cell is positioned within the cavity and is substantially concentrically aligned with respect to the inlet port.

70 Claims, 6 Drawing Sheets

US 7,855,027 B2

METHODS AND APPARATUS FOR BREATH ALCOHOL TESTING

CROSS REFERENCE TO RELATED APPLICATIONS

This application claims priority to and the benefit of the filing date of U.S. Provisional Application No. 60/504,448 filed on Sep. 19, 2003, and claims the priority of PCT International Patent Application Number PCT/US2004/30793, filed Sep. 17, 2004, both of which are hereby incorporated by reference in its entirety.

BACKGROUND OF THE INVENTION

This invention relates generally to breath alcohol testing and, more particularly, to a sampling system and fuel cell configuration for a breath alcohol tester.

Known breath testers include a sampling assembly, fuel cell assembly, and electronics/software for determining an amount of alcohol in a sample, based on a signal generated by a fuel cell. More specifically, the sampling assembly functions to deliver a controlled volume breath sample to the fuel cell assembly, and the fuel cell generates a signal representative of the amount of alcohol in the delivered sample. The fuel cell should react quickly and completely to the introduction of an alcohol sample of controlled volume, and produce electrons with repeatability in response to the reaction with the alcohol. The number of electrons produced is proportional to the concentration of alcohol consumed by the reaction. The signal generated by the fuel cell is processed by the electronics/software to determine alcohol concentration.

At least some known sampling assemblies include a pump connected to the fuel cell assembly via a tube. The pump pulls a breath sample into the fuel cell housing through a sampling port, across the face of the fuel cell, and out the opposite side of the housing, through the pump, and into the ambient air. Other known sampling assemblies include a cylinder and piston directly attached to the fuel cell assembly. Within such configurations, the sampling assembly and the fuel cell assembly are coupled together in flow communication via a small opening, such that the piston draws a breath sample into the fuel cell, through a sampling port, and into the cylinder, through the small opening. More specifically, within such a configuration, the fuel cell assembly includes two ports and is sometimes referred to as a bypass system.

However, with at least some known bypass systems, it may be difficult to ensure that a consistent and approximately equal volume is sampled each time because of the pump or piston operation. Moreover, with at least some bypass systems, it may be difficult to ensure that 100% of the alcohol in the sample is consumed by the fuel cell during a measurement. As such, any alcohol that originally bypassed the fuel cell going through the fuel cell may start a new reaction in the fuel cell upon reset, thus extending the time between subsequent tests.

In another known configuration, the sampling assembly is directly connected to the fuel cell assembly, and the sampling assembly includes a moveable element, such as a diaphragm. When the sampling assembly is attached to the fuel cell assembly, the diaphragm functions as a moveable wall of the fuel cell housing. Accordingly, when the diaphragm moves in one direction, a breath sample is drawn into the fuel cell assembly, but not through it. This type of assembly in which the fuel cell assembly has only one port is sometimes referred to as a dead-end system.

However, with at least some known dead-end systems, when diaphragms are used, the diaphragm assumes its natural molded shape in the "sample" position, such that when the diaphragm is in the reset position, stresses may be induced into the diaphragm material depending on the material. Over time, such stresses can alter the shape of the reset diaphragm which may adversely affect the long term calibration of the sampling assembly.

BRIEF DESCRIPTION OF THE INVENTION

In one aspect, a fuel cell assembly is provided. The assembly includes a fuel cell, a fuel cell housing, and a diaphragm. The fuel cell housing includes an endwall and an inlet port extending through said endwall. The inlet port is for admitting a breath sample into the housing. The diaphragm is coupled within the housing such that a cavity is defined between the housing and the diaphragm. The fuel cell is positioned within the cavity and is substantially concentrically aligned with respect to the inlet port.

In another aspect, an assembly is provided. The assembly includes a fuel cell housing, a fuel cell, and an actuator. The fuel cell housing has a centerline extending therethrough, and includes an inlet port extending through and concentrically aligned with respect to the housing. The fuel cell is positioned within the cavity such that the fuel cell is substantially concentrically aligned with respect to the housing. The fuel cell includes an opening extending therethrough and concentrically aligned with respect to the fuel cell for admitting a breath sample into the housing. The actuator is removably coupled to the housing.

In a further aspect, a fuel cell housing assembly is provided. The fuel cell housing assembly includes a fuel cell housing defining a cavity, therein, and a fuel cell including an outer surface, an inner surface, and an opening extending therebetween. The opening is substantially concentrically aligned with respect to the fuel cell for permitting a breath sample to be drawn into the cavity and dispersed substantially evenly across the fuel cell.

DETAILED DESCRIPTION OF THE INVENTION

Figure 1:
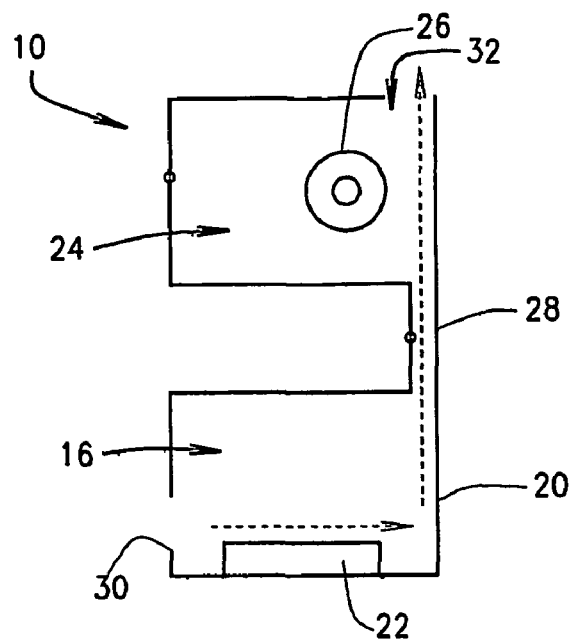
FIG. 1 is a schematic illustration of an exemplary known bypass sampling system that may be used with a breath tester.

In the breath tester industry, several design considerations may impact the performance of the breath tester. For example, accuracy, reliability, cost, long life, radio frequency interference (RFI) immunity, quick processing, and low energy usage typically are considerations when selecting a breath alcohol tester. Other factors may include the amount of time that must elapse between subsequent tests (known as the testing cycle time) and long term calibration stability. In order to achieve these objectives, generally manufacturers attempt to balance/optimize several design considerations which will be discussed in more detail below.

Fuel Cell and Gas Sample Chamber

Fuel cells used with sampling assemblies can be viewed as batteries that produce electrical energy from a fuel. In a measuring application, the measured volume of fuel should be consumed as quickly as possible and the electron-producing reaction should finish as quickly as possible. Also, all the alcohol molecules should begin their chemical conversion at the same time when the sample is introduced. Otherwise, some molecules begin their reaction later than others and the time to completion of the overall reaction is extended in time.

The efficiency and expedience of the chemical conversion of the alcohol molecules may be dependent upon a height of headspace defined in a fuel cell assembly. During breath testing, the breath sample resides in the headspace. Accordingly, a smaller headspace facilitates providing each alcohol molecule in the breath sample an opportunity to contact the electrode surface as quickly as any other molecule, as the breath sample enters the fuel cell headspace from an inlet sample port. Known fuel cell assemblies therefore should have a minimum headspace height.

Typically, because of the orientation of the fuel cell within the fuel cell assembly, a portion of the fuel cell closest to the inlet sample port will generally be involved in alcohol reactions 100% of the time, while a portion of the fuel cell furthest away from the inlet sample port generally is not fully utilized. As such, to counter such flow effects, at least some known bypass system sampling assemblies position baffles in the breath sample flow path in an attempt to more evenly distribute the alcohol molecules in the breath sample across the fuel cell. However, known baffles may not increase the amount of the fuel cell being utilized during testing.

Moisture Content

Another design factor is that the ambient environmental moisture content of air may cause undesirable issues within the fuel cell assembly when allowed to be in continuous communication with the sampling assembly's internal environment that contains the fuel cell. Generally, fuel cells are fabricated with an electrolyte having a concentration that is approximately in equilibrium with an "average" ambient relative humidity (approximately 45%-60%). However, the environment may stray from this average relative humidity at any point in time, to some level above, or below, the average. Moreover, in some extreme environments, the relative humidity can range from close to 0% to close to 100%. As a result, the fuel cell either wants to "give up," or "take on" moisture whenever environmental humidity differs from the cell equilibrium value and the two environments are in communication, such as through a sample inlet.

When breath samples or wet simulator samples (both at approximately 100% relative humidity) enter a fuel cell and are then expelled after the alcohol is consumed, some amount of moisture may be added to the cell. Similarly, when a dry gas sample (at approximately 0% relative humidity) enters a fuel cell and is expelled, a small amount of moisture may be removed from the fuel cell. These two types of samples tend to balance each other to some degree, and as such, generally do not create issues of the same magnitude as compared to the issues that may be created by the long term environmental equilibrium effects. Large changes in moisture content of the fuel cell electrolyte may result in a fuel cell failure, result in less fuel cell repeatability, slow the fuel cell reaction, add to long term calibration drift, and/or cause inaccurate readings.

To facilitate reducing the effects of a relatively unstable moisture content, several known approaches have been utilized. Within one such approach, the size of the inlet hole to the fuel cell through which breath samples must travel to the active area of the fuel cell is minimized. These inlet holes are typically sealed between tests. By forming the inlet holes as small as possible, during idle periods of time between tests, the inlet hole presents only a small diffusion path for moisture exchange between the fuel cell and the environment. Changes in ambient atmospheric pressure may actually produce a flow of air between the fuel cell and the environment, also causing a moisture exchange. However, if the sampling inlet hole is too small, the risk of the inlet freezing closed with ice during cold condensing conditions is increased. In addition, with a smaller inlet hole, a longer period of time is required for the breath sample to enter the cell, and more power is required to draw a breath sample through the hole. In addition, diffusion through a small inlet hole may still contribute to the moisture exchange between the fuel cell and the environment.

To additionally facilitate reducing the effects of radically changing moisture content, other known fuel cell housings have been fabricated from materials that possess characteristics of low water transmission. More specifically, such materials generally inhibit the transmission of moisture. However, such materials generally increase the overall assembly costs of the sampling assembly.

Another known approach that has been utilized to facilitate reducing the effects of the moisture content, is to attempt to close off the inlet with an edge of the flexible diaphragm that also serves as the main sampling mechanism element. However, because the inlet seal is at the edge of the diaphragm where little direct force may be applied to uncover the inlet, suction forces may inhibit opening the inlet for the next breath sample.

Control of the Sample Volume

The operation of the breath tester may also be dependent on controlling the sample volume within the sampling assembly. For example, in a mechanical sampling system, as a movable element, such as a piston, diaphragm, or other actuator, translates from a "start" position to an "end" position, a breath sample is drawn into the fuel cell headspace volume for measurement. As described in U.S. Pat. No. 5,291,898, the movable element should ideally start and stop in the exact same location every time to facilitate ensuring that the same volume of gas is sampled during each testing operation. More specifically, within at least some known sampling assemblies, rigid mechanical stops in each direction facilitate ensuring that the same volume of gas is sampled each time. In addition, the effects of mechanical wear should be minimized over time such that the volume of the sample remains approximately consistent. These principles are the same for a dead-end system and for a bypass system. After a measurement is taken, the mechanism returns to the "start" position to be ready for the next sample.

However, known bypass systems that utilize a piston with a crankshaft may be difficult to configure to ensure that a consistent and equal volume is sampled each time. Accordingly, with known bypass systems that utilize a piston, sensors are generally relied upon to start and stop movement of the piston because of the rotary motion in one direction of the crank. Such sensors generally increase the costs and complexity of the fuel cell assembly. With pumps, an amount of run time typically is used to determine volume pumped through the fuel cell headspace. In some dead-end systems, the flexible diaphragm actually forms a moveable wall within the fuel cell assembly, and thus, defines the headspace volume within the fuel cell. In the "start" position, the headspace volume above the fuel cell is attempted to be minimized such that the "end" position can also remain as close to the fuel cell as possible during testing. More specifically, although the "end" position should represent a significant increase in the headspace volume above the fuel cell, ideally, in the "end" position, the height of the volume above the fuel cell should be minimized so as to keep alcohol molecules as close as possible to the active surface. In bypass systems (with no moveable wall), a constant headspace volume is maintained over the fuel cell.

Sample Molecule Consumption

As described in U.S. Pat. No. 4,487,055, another design consideration is ensuring that 100% of the alcohol in the breath sample is consumed by the fuel cell during a testing measurement. Known bypass systems may present some issues in ensuring that 100% of the alcohol in the sample is consumed by the fuel cell during a measurement. Specifically, upon re-setting, the amount of sample that originally bypassed the fuel cell is blown back out through the fuel cell chamber and back through the inlet hole. Any alcohol that originally bypassed the fuel cell may actually start a new reaction in the fuel cell as the bypassed alcohol is channeled back over the fuel cell as the system is reset. The additional reactions extend the time that must elapse between subsequent tests.

Generally, regardless of the sampling assembly utilized, within breath testers, there should be no sample "by-pass" of any of the alcohol, such that any remnant alcohol is prevented from being re-introduced to the fuel cell during re-setting or recycling of the mechanical sampling system. Such "by-pass alcohol" could cause an additional fuel cell reaction to undesirably start and/or complete, thus delaying the time until the next valid sample is obtainable.

Various approaches have attempted to facilitate controlling consumption of the alcohol within the sample. For example, within at least some known breath testers, the breath sample is drawn through the fuel cell assembly in only one direction past the fuel cell, i.e., the sample enters the fuel cell, exits the fuel cell, enters a pump, and is discharged from the pump all in a generally linear direction. However, within such breath testers, it may be difficult to ensure that the sample size drawn through the fuel cell is substantially constant every time.

Within other known breath testers, a reset mechanism is reset almost immediately after a breath sample enters the fuel cell assembly. As a result, however, the sample may be exhausted back through the inlet sample port even before the fuel cell reaction is complete. Accordingly, with such a system, it may be difficult to ensure that the percentage of total alcohol in the sample that attaches to the fuel cell surface remains substantially constant over time.

Moreover, as a fuel cell ages, and when the fuel cell is exposed to alcohol, it may take longer for the alcohol molecules to attach to the fuel cell active surface. Thus, in a bypass system, the number of alcohol molecules that may bypass the reaction changes as the fuel cell ages. Accordingly, the long term calibration stability of such systems may be affected.

Electronics and Software

Generally, there are two known methods for reading the fuel cell signal via electronics and software. One such method is known as the peak method, and the other method is known as the integral method. There are numerous known software methods that use the basic methods of either peak or integral readings, and then use various methodologies to attempt to obtain a final measurement more quickly without diminishing the accuracy of the measurement.

The peak method generally measures the rate of reaction, whereas the integral method measures the total number of electrons produced by the reaction. The integral method and associated circuitry is generally the faster, more accurate, and more stable method of measurement, as described in U.S. Pat. No. 4,770,026. Additionally, the accuracy of the integral method is believed to be less easily compromised with methods that facilitate increasing the speed of analysis. However, under the variety of conditions that may occur when using a breath testing instrument such as temperature, humidity, frequency and spacing of tests, and age, generally the pure integral method provides a more accurate measurement system over the long term. Thus, design changes that can be done via sampling techniques and fuel cell construction that contribute to the speed and repeatability of the pure integral method may represent an important and reliable improvement in the state-of-the-art.

Heating

Generally it is known that heating the fuel cell and sampling assembly may be beneficial in certain situations. For example, heating the fuel cell may facilitate causing the chemical reaction in the fuel cell to occur more efficiently and faster. Heating also generally allows the instrument to avoid issues that may be associated with a temperature coefficient of the signal of interest due to temperature effects on the fuel cell and/or associated mechanical and electrical parts across varying temperatures.

Heating, however, requires additional power and may adversely limit the battery life. Heating also generally results in requiring additional instrument warm-up time than would otherwise be necessary. Nonetheless, at least some known systems use a disc or semiconductor heater coupled against one side of the fuel cell housing. However, such a design may cause thermoelectric signals to be generated in the fuel cell as a result of a thermal gradient induced across the fuel cell. Such thermoelectric signals may degrade the accuracy of the fuel cell.

Other known systems use an external heater (pouch or stand) to facilitate heating the entire breath testing instrument to a substantially uniform temperature. However, such heaters generally require much more power than is normally desired in a handheld instrument, and as such, instruments including such heaters generally require large batteries or an external voltage source, such as a voltage supply in a car or building. As a result, this type of heater may limit the freedom of how a handheld instrument can be used.

Uniform heating of the fuel cell assembly and sampling assembly can produce positive results, but such heating may also add to the rate at which the fuel cell loses moisture to the environment in a system where the fuel cell is not sealed off from the environment between tests. This effect can be mitigated somewhat by only heating the instrument when a test is to be run, but in doing so, the warm-up times prior to executing a test are generally extended.

Figure 2:
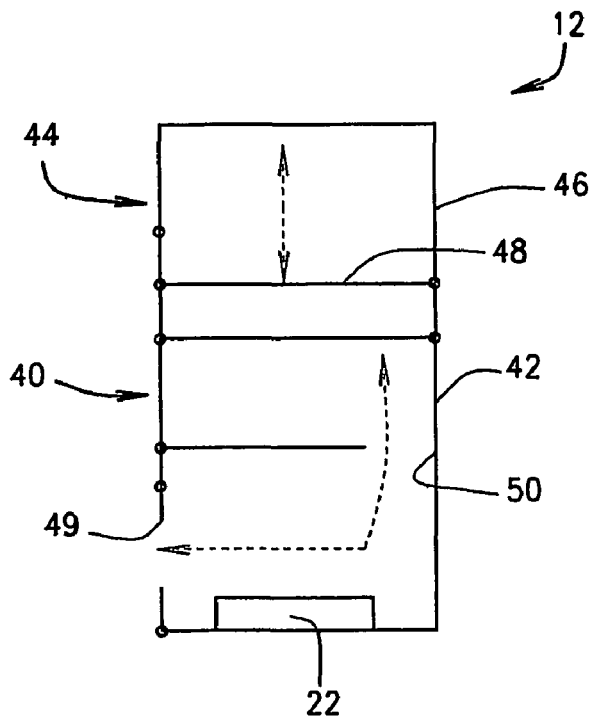
FIG. 2 is a schematic illustration of an embodiment of another known bypass sampling system that may be used with a breath tester.
Figure 3:
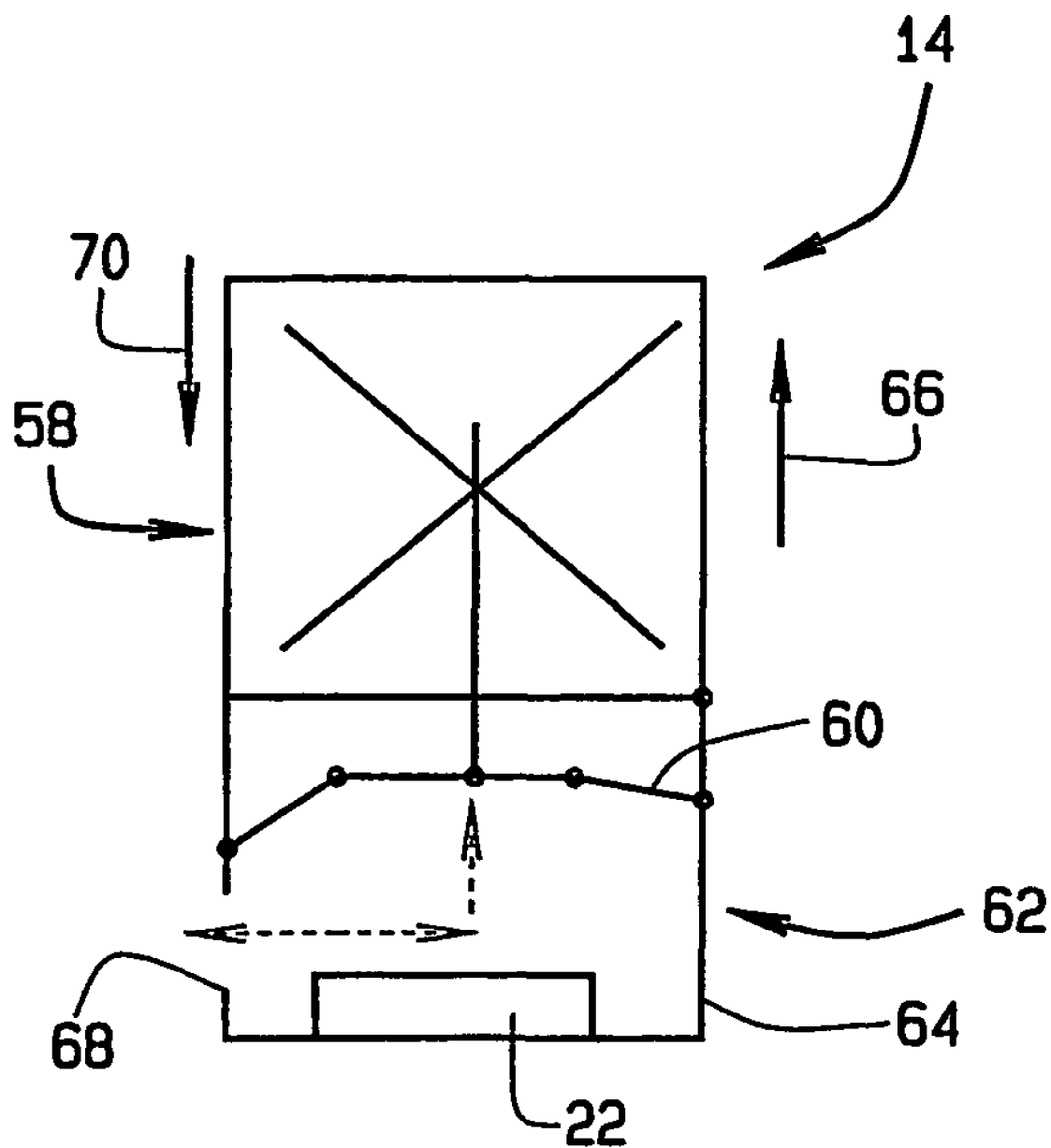
FIG. 3 is a schematic illustration of an exemplary known dead-end sampling system that may be used with a breath tester.

FIG. 1 is a schematic illustration of an exemplary known bypass sampling system 10 that may be used with a breath tester. FIG. 2 is a schematic illustration of an embodiment of another known bypass sampling system 12 that may be used with a breath tester. FIG. 3 is a schematic illustration of an exemplary known dead-end system sampling system 14 that may be used with a breath tester. Sampling systems 10, 12, and 14 were designed taking into account many of the design considerations described above, and as such, each may also be subjected to many of the problems and issues also described above.

Bypass sampling system 10 includes a fuel cell assembly 16 including a housing 20 that contains a fuel cell 22 therein, and a sampling mechanism 24. Sampling mechanism 24 includes a pump 26 and is coupled to fuel cell assembly 16 via a connecting tube 28. During testing, operation of pump 26 causes a breath sample to be drawn into fuel cell housing 20 though a sampling port 30 formed in a wall of housing 20. More specifically, pump 26 causes the breath sample to be drawn across an exposed face of fuel cell 22, towards the opposite side of housing 20. The breath sample is then drawn into pump 26 through tube 28 wherein the sample is discharged from sampling assembly 10 through a discharge port 32.

Bypass sampling system 12 also includes a fuel cell assembly 40 including a housing 42 that contains fuel cell 22 therein, and a sampling mechanism 44. Sampling mechanism 44 includes a cylinder 46 and piston 48 that are coupled to fuel cell assembly 40. More specifically, sampling mechanism 44 is coupled in flow communication with fuel cell assembly 40 via an opening 50. During testing, operation of piston 48 causes a breath sample to be drawn across fuel cell 22 through a sampling port 49 formed within a sidewall of housing 42, and into cylinder 46 through opening 50.

Dead-end sampling system 14 includes a sampling mechanism 58 including a moveable element 60 and a fuel cell sub-assembly 62 including a housing 64 that contains fuel cell 22 therein. In the exemplary embodiment, moveable element 60 is a diaphragm. Sampling mechanism 58 is coupled to fuel cell assembly 62 such that diaphragm 60 functions as a moveable wall defining fuel cell housing 64. Accordingly, during testing, when diaphragm 60 is moved in a first direction, represented by arrow 66, a breath sample is drawn into fuel cell assembly 62 through a sample port 68 formed along a sidewall of housing 64. When diaphragm 60 is moved in an opposite second direction, represented by arrow 70, the breath sample is forcibly discharged from housing 64 through port 68.

Figure 4:
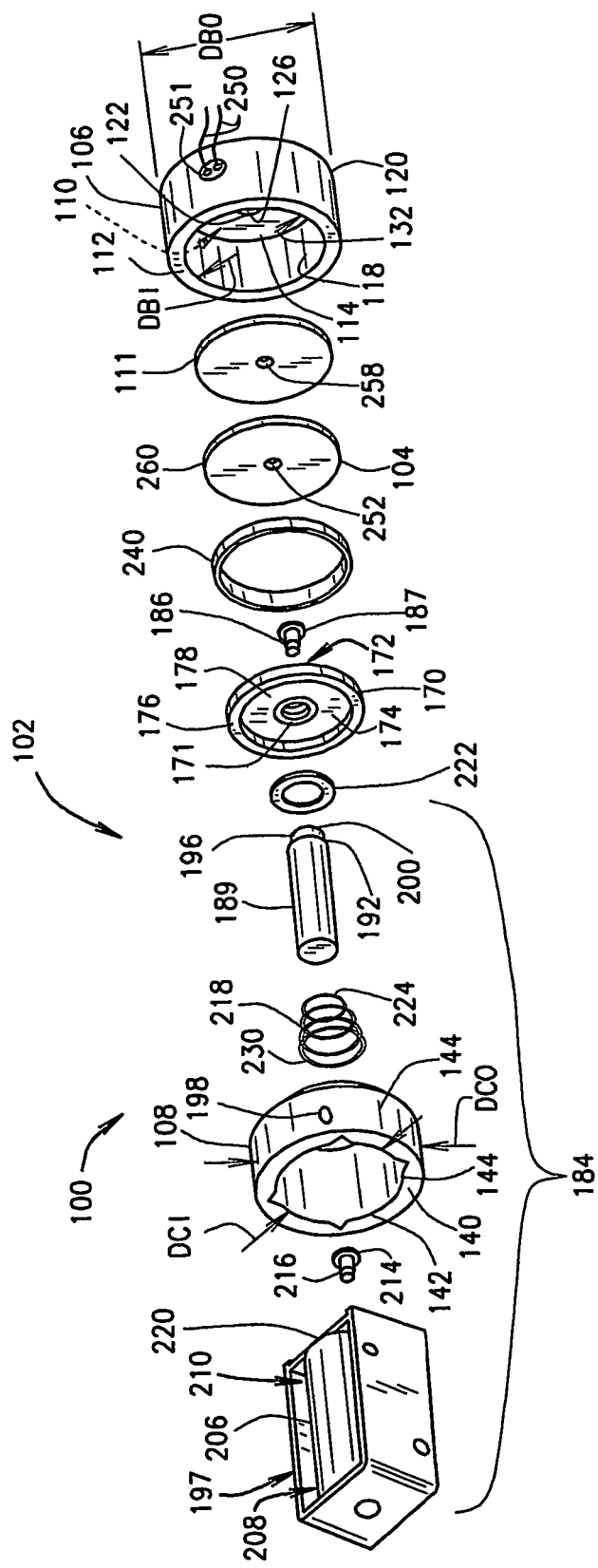
FIG. 4 is an exploded view of an exemplary sampling system.
Figure 5:
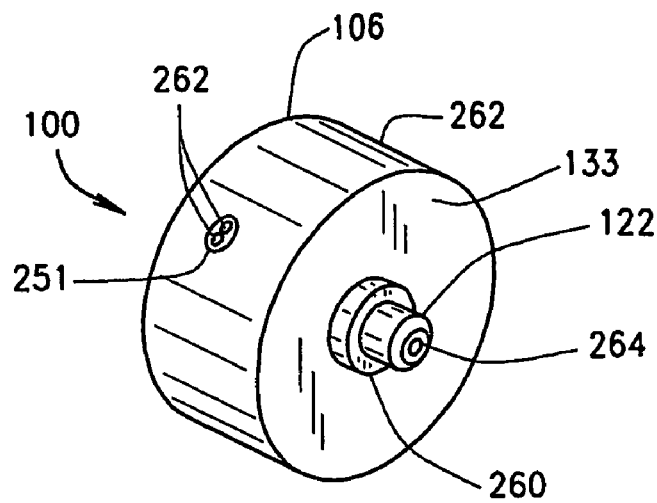
FIG. 5 is an enlarged perspective rear view of a portion of the sampling system shown in FIG. 4.
Figure 6:
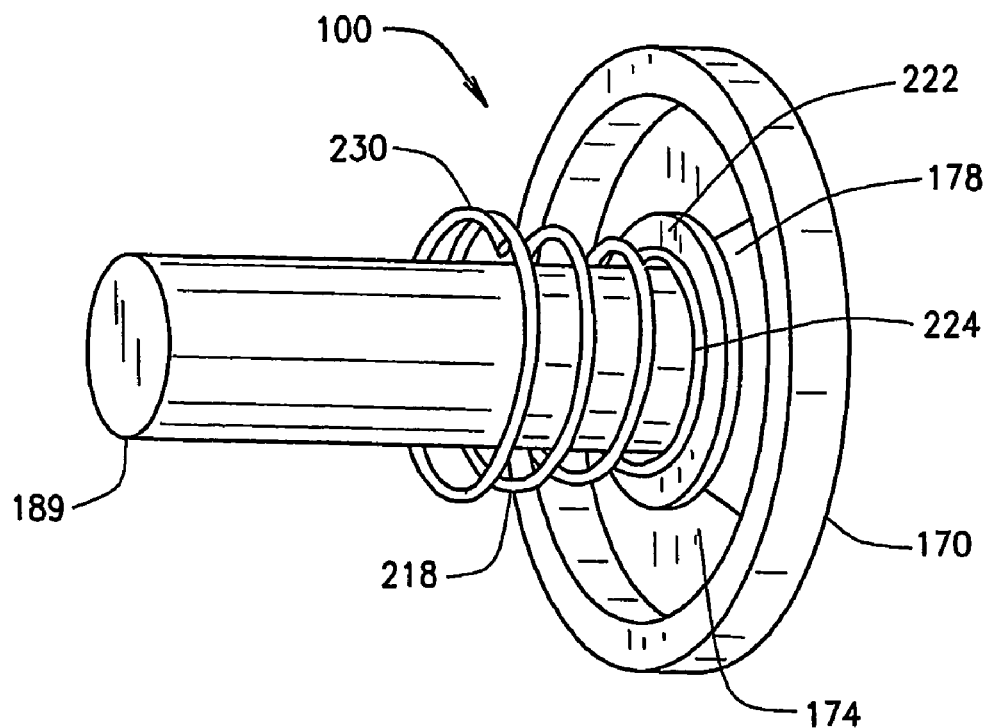
FIG. 6 is an enlarged perspective view of an assembled portion of the sampling system shown in FIG. 4.
Figure 7:
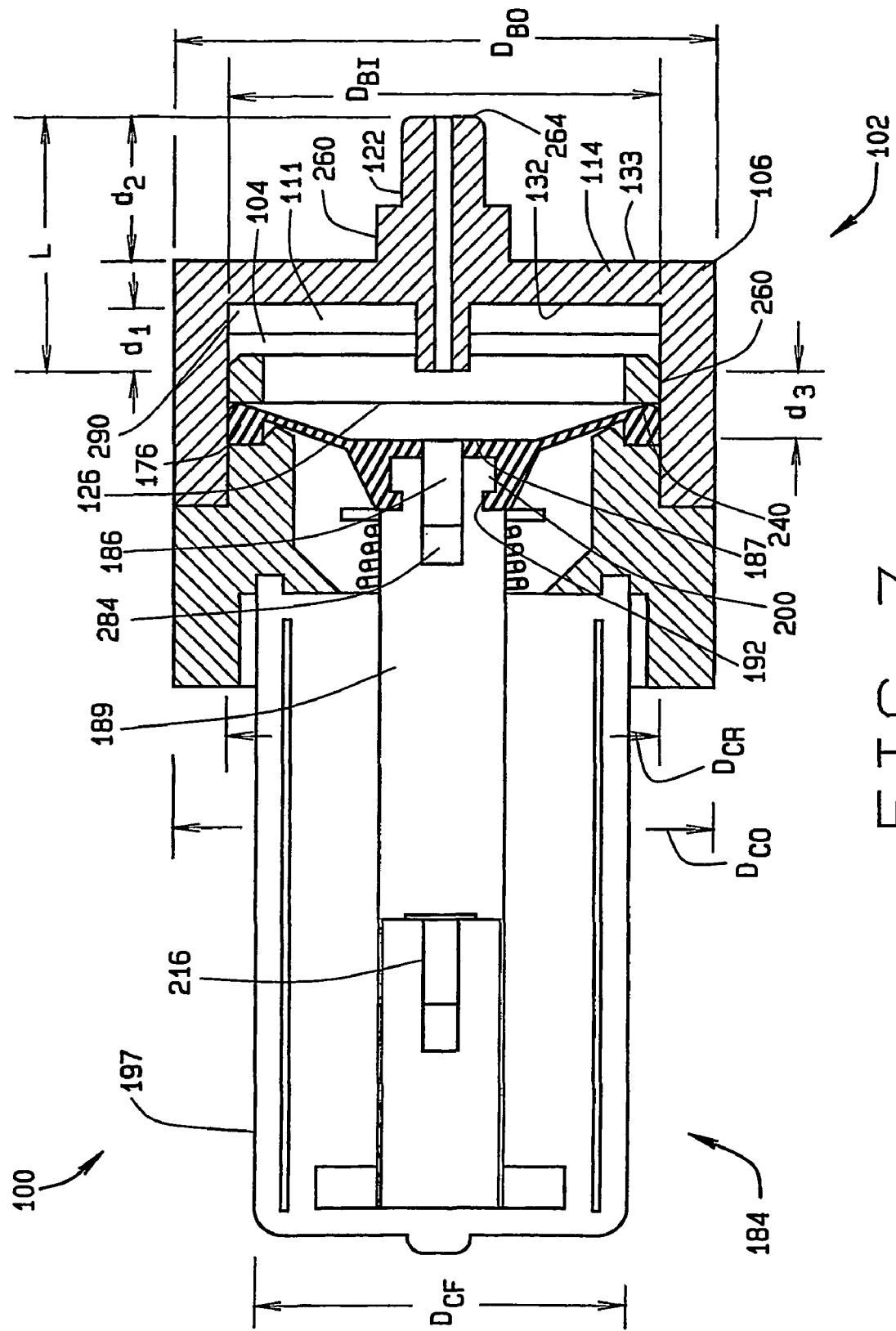
FIG. 7 is a cross-sectional view of the sampling system shown in FIG. 4 and in a sampling mode of operation.
Figure 8:
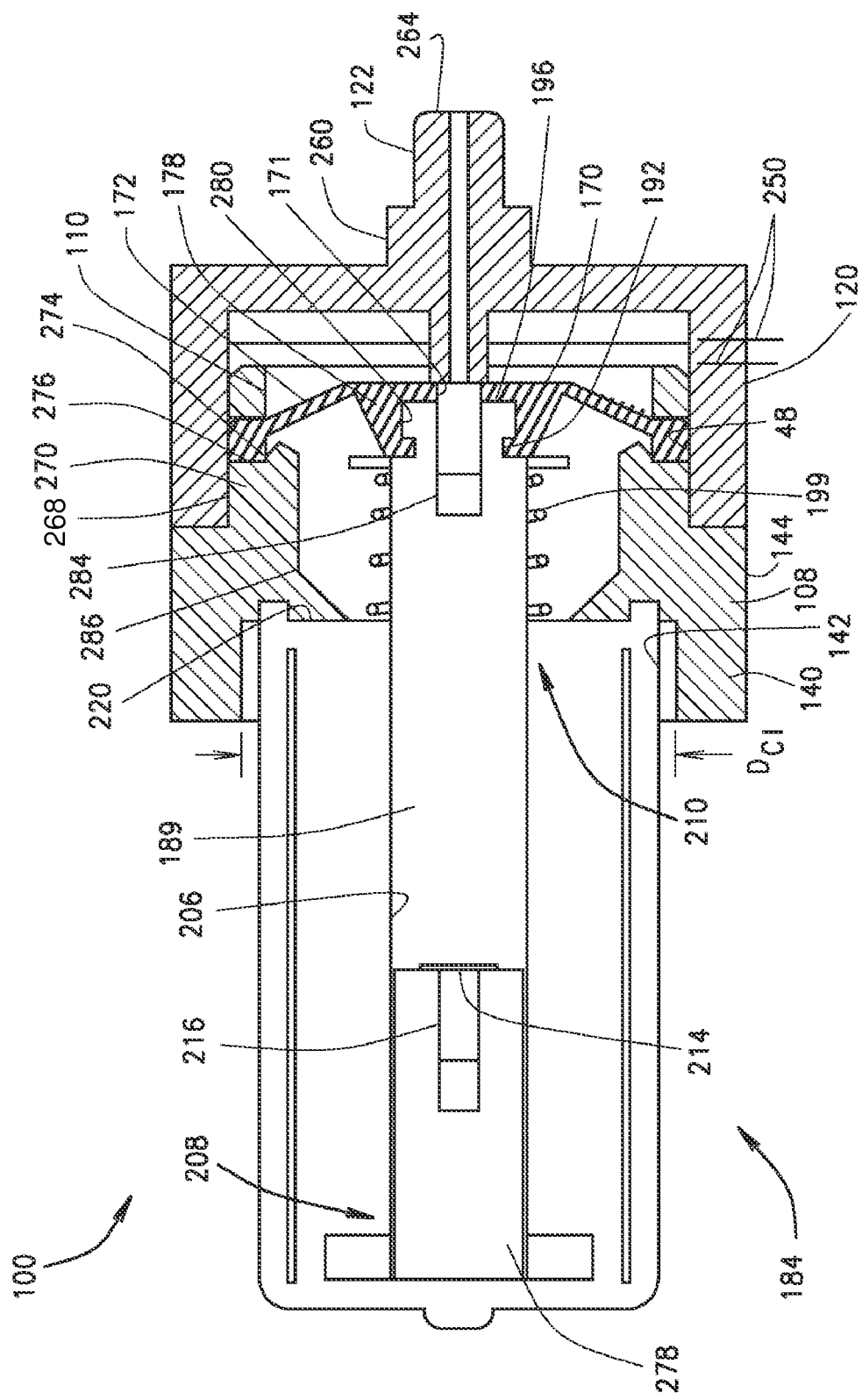
FIG. 8 is a cross-sectional view of the sampling system shown in FIGS. 4 and 5 and in a reset mode of operation.

FIGS. 4-8 illustrate various aspects of an exemplary sampling system 100 in accordance with one embodiment of the present invention. Specifically, FIG. 4 is an exploded view of sampling system 100, and FIG. 5 is an enlarged perspective rear view of a portion of sampling system 100. FIG. 6 is an enlarged perspective view of an assembled portion of sampling system 100, and FIGS. 7 and 8 are respective cross-sectional views of sampling system 100 positioned in a sampling mode of operation and in a reset mode of operation. As shown in FIG. 4, sampling system 100 is a dead end sampling system that includes a fuel cell housing assembly 102 and a fuel cell 104 positioned therein. In the exemplary embodiment, housing assembly 102 is a multi-piece assembly that includes a base portion 106 and a coupling portion 108 that are removably coupled together such that a substantially air-tight cavity or chamber 110 is defined within housing assembly 102. In one embodiment, housing assembly portions 106 and 108 are molded from a plastic material. Fuel cell 104 and a backup disk 111, described in more detail below, are contained within cavity 110.

In the exemplary embodiment, housing base portion 106 includes a sidewall 112 that extends from, and circumscribes, a substantially circular base 114. In alternative embodiments, base 114 is non-circular and/or sidewall 112 does not extend substantially perpendicularly from base 114. Accordingly, in the exemplary embodiment, base portion 106 has an inner diameter $D_{BI}$ measured with respect to an inner surface 118 of sidewall 112, and an outer diameter $D_{BO}$ measured with respect to an outer surface 120 of sidewall 112.

Sidewall 112 is formed with a substantially smooth inner surface 118 that, as described in more detail below, enables housing base portion 106 to removably couple to housing coupling portion 108.

A hollow inlet tube 122 extends through base 114. In the exemplary embodiment, inlet tube 122 has a substantially circular cross-section and is substantially concentrically aligned with respect to base 114. More specifically, in the exemplary embodiment, inlet tube 122 extends substantially concentrically through base 114 such that a radially inner end 126 extends a distance $d_1$ (shown in FIG. 7) inward from an inner surface 132 of base 114. In the exemplary embodiment, base 114 is formed integrally with inlet tube 122. Inlet tube 122, as described in more detail below, enables a breath sample to enter fuel cell housing assembly 102 for reaction. Air also is expelled from inlet tube 122 after analysis.

In the exemplary embodiment, housing coupling portion 108 includes a sidewall 140 that has an inner surface 142 that defines an inner diameter $D_{CI}$ and an outer surface 144 that defines an outer diameter $D_{CO}$ for coupling portion 108. In the exemplary embodiment, outer diameter $D_{CO}$ is approximately equal to housing base portion outer diameter $D_{BO}$. In an alternative embodiment, outer diameter $D_{CO}$ is larger than housing base portion outer diameter $D_{BO}$. In a further alternative embodiment, outer diameter $D_{CO}$ is smaller than housing base portion outer diameter $D_{BO}$.

A moveable flexible diaphragm 170 is removably coupled within fuel cell housing base portion 106. Diaphragm 170 is continuous with the exception of a single substantially circular penetration 171, such that when diaphragm 170 is clamped within fuel cell housing base portion 106, diaphragm 170 creates an air-tight cavity 110 within housing portion 106 and between base 114 and diaphragm 170. More specifically, in the exemplary embodiment, diaphragm 170 is substantially circular, and includes a base side 172 and an opposite actuator side 174. Alternatively, diaphragm 170 is continuous and includes no penetrations such as penetration 171.

Diaphragm base side 172 is continuous, with the exception of penetration 171, and diaphragm actuator side 174 includes a rim 176 and a substantially cylindrical hub 178. Rim 176 extends outward from side 174 and enables diaphragm 170 to be coupled within housing base portion 106, and hub 178 extends radially outward from actuator side 174. More specifically, rim 176 provides a flexible element that enables diaphragm 170 to be coupled within housing base portion 106, as described herein. In an alternative embodiment, diaphragm base side 172 remains continuous, but is formed with at least a portion of hub 178. In the exemplary embodiment, diaphragm hub 178 is aligned substantially concentrically with respect to diaphragm 170 and is formed with an undercut (not shown in FIG. 4) that facilitates diaphragm 170 being coupled to an actuator 184, as described herein.

In the exemplary embodiment, a flat-headed pin 186 having a top face 187 is inserted substantially concentrically through diaphragm penetration 171. Pin 186 is retained by a press-fit within a recess (not shown in FIG. 4) formed in one end of an armature 189 of actuator 184. More specifically, when pin 186 is fully inserted, face 187 is substantially flush with diaphragm base side 172.

Actuator armature 189 is formed with a recessed portion 192 that circumscribes armature 189 adjacent an end 196 of armature 189. In the exemplary embodiment, armature 189 is fabricated from a ferrous material. In the exemplary embodiment, the frame 197 of actuator 184 enables actuator 184 to be rigidly coupled to fuel cell housing assembly 102. More specifically, in the exemplary embodiment, during assembly, actuator 184 is press-fit and glued into coupling portion 108.

In alternative embodiments, coupling portion 108 is customized for use with other actuators and/or actuating devices. In other alternative embodiments, coupler portion 108 and the actuator 184 are both rigidly mounted to a third member. In the exemplary embodiment, coupling portion 108 includes a vent hole 198 which facilitates ensuring that a cavity 199 defined within coupling portion 108 is never sealed, thus preventing a build up of pressure against which diaphragm 170 has to overcome to move during sampling, as is described in more detail below. In other alternative embodiments, actuator 184 is coupled to housing assembly 102 in such a manner such that cavity 199 remains vented, and as such, vent hole 198 is not required. In yet further alternative embodiments, vent hole 198 is not formed within coupling portion 108, but rather is positioned to facilitate preventing cavity 199 from becoming pressurized.

In the exemplary embodiment, actuator 184 includes a cylindrical receiver 206 in which armature 189 is movable from one end 208 of receiver 206 to the other end 210 depending on the direction of current flow through an electrical coil (not shown) embodied in actuator 184. At the base of receiver 206 is a permanent magnet (not shown in FIG. 4) which retains armature 189 against a head 214 of a pin 216 while working against force induced by a compressed tapered spring 218 in the sample position, as shown in FIG. 7. In an alternative embodiment, system 100 does not include a magnet. Spring 218 is always compressed to some degree between a face 220 of actuator 184 and a washer 222. Washer 222 facilitates preventing a smaller diameter end 224 of spring 218 from pressing into, or around, diaphragm hub 178 while a larger diameter end 230 of spring 218 remains in contact against actuator face 220. In an alternative embodiment, spring 218 is not tapered.

A rigid clamp ring 240 extends between diaphragm 170 and fuel cell 104. In the exemplary embodiment, clamp ring 240 is a toroidal body that extends continuously circumferentially. Clamp ring 240, as described in more details below, facilitates retaining components of sampling system 100 together. In the exemplary embodiment, and as described in more detail below, clamp ring 240 facilitates ensuring clearance for fuel cell wires 250 exiting fuel cell housing assembly 102 through a counterbore 251 and small openings 262 formed in housing base portion 106.

In the exemplary embodiment, fuel cell 104 is substantially circular and includes an opening 252 that extends through fuel cell 104 and is aligned substantially concentrically with respect to fuel cell 104. Alternatively, opening 252 is not aligned substantially concentrically with respect to fuel cell 104. Also, in the exemplary embodiment, backup disk 111 is substantially circular and includes an opening 258 extending substantially concentrically therethrough. Openings 252 and 258 are sized to receive inlet tube end 126 therethrough such that fuel cell 104 may, be positioned against backup disk 111, which in turn may be positioned against base inner surface 132 while surrounding inlet tube 122. An active face 260 of fuel cell 104 faces away from the direction from which the breath sample is drawn, such that the breath sample enters from the center of fuel cell 104 and extends substantially uniformly to the outer periphery of fuel cell 104. It should be noted, that the present invention is not directed to the composition of fuel cell 104 nor backup disk 111.

FIG. 5 is an enlarged perspective rear view of a portion of sampling system 100. Specifically, FIG. 5 is an enlarged rear view of fuel cell housing base portion 106. As described above, inlet tube 122 extends through base 114 (shown in FIG. 4), and in the exemplary embodiment, inlet tube 122 has a substantially circular cross-section and is substantially concentrically aligned with respect to base 114. More specifically, in the exemplary embodiment, inlet tube 122 extends substantially concentrically through a boss 260 extending outwardly from an outer surface 133 of base 114. In alternative embodiments, base 114 does not include boss 260. Inlet tube 122 has a length (not shown in FIG. 5) that enables a radially outer end 264 of tube 122 to extend a distance (not shown in FIG. 5) outward from base outer surface 133. Tube radially outer end 264 typically protrudes into a mouthpiece or other manifold where the gas to be sampled is present. In the exemplary embodiment, base 114 is formed integrally with boss 260 and with inlet tube 122.

FIG. 6 is an enlarged perspective view of an assembled portion of sampling system 100. Specifically, FIG. 6 illustrates an assembled perspective view of armature 189 coupled to diaphragm 170. During assembly, a tip portion 200 (shown in FIG. 4) of armature 189, defined as the area of armature 189 that extends between armature end 192 and recessed portion 196 (shown in FIG. 4), is inserted within diaphragm hub 178 such that the tip portion 200 engages an undercut (not shown in FIG. 6) formed in diaphragm hub 178. Armature recessed portion 196 enables movable armature 189 to be rigidly coupled to fuel cell housing assembly 102 (shown in FIG. 4) within the hub undercut, as is described in more detail below. In one embodiment, an adhesive is used to secure armature 189 within hub 178. Accordingly, in at least some embodiments, because diaphragm base side 172 is continuous, actuator mounting does not impact whether fuel cell housing assembly 102 is an air-tight sealed assembly. More particularly, in the exemplary embodiment, fuel cell housing assembly 102 is sealed air-tight independently from actuator 184.

Washer 222 extends circumferentially around armature 189 and when sampling system 100 is fully assembled, washer 222 is positioned between spring 218 and diaphragm 170. More specifically, washer 222 extends between spring 218 and diaphragm 170 to facilitate preventing spring end 224 from pressing into, or around, diaphragm hub 178.

FIGS. 7 and 8 are respective cross-sectional views of sampling system 100 positioned in a sampling mode of operation and in a reset mode of operation. Inlet tube 122 extends through base 114 and has a length L that enables tube radially inner end 126 to extend a distance d1 inward from base inner surface 132, and tube radially outer end 264 to extend a distance d2 from base outer surface 133.

Coupling portion 108 includes a coupling ring 270 that has an outer diameter $D_{CR}$ that is slightly smaller than a diameter $D_{BI}$ of housing base portion surface 118. Accordingly, when housing assembly 102 is fully assembled, as described in more detail below, coupling ring 270 is received in a press-fit arrangement within housing base inner surface 118. In an alternative embodiment, coupling ring 270 is received in a different fit arrangement, such as, but not limited to, a slip-fit arrangement, or an interference fit arrangement.

Coupling ring 270 is formed with an offset 274 that has a diameter DCF that is smaller than coupling ring diameter outer diameter DCR such that a substantially planar area 276 is defined between offset 274 and an outer surface 268 of coupling ring 270.

Diaphragm 170 is removably coupled within fuel cell housing base portion 106. Specifically, in the exemplary embodiment, diaphragm hub 178 is aligned substantially concentrically with respect to diaphragm 170 and is formed with an undercut 280 that facilitates diaphragm 170 being coupled to actuator 184. More specifically, pin 186 is inserted substantially concentrically through diaphragm penetration 171 and is retained by a press-fit within a recess 284 formed in one end of actuator armature 189.

When pin 186 is fully inserted through diaphragm penetration 171, pin face 187 is substantially flush with diaphragm base side 172. Because face 187 is hardened in comparison to diaphragm 170, face 187 provides a more solid surface for inlet tube end 126 to contact when diaphragm 170 is in the reset position (shown in FIG. 8). As such, face 187 facilitates preventing the softer diaphragm 170 from "deforming around" or "molding around" inlet tube end 126 when diaphragm 170 remains in the reset period for extended periods of time. Without face 187, such diaphragm deformations around inlet tube end 126 could cause diaphragm 170 to become inadvertently stuck against inlet tube end 126. Over time, such diaphragm deformations could also undesirably alter a hard stop reset position of diaphragm 170, as described in more detail below. In one alternative embodiment, pin 186 and armature 189 are fabricated integrally together. In other alternative embodiments, pin 186 is not concentrically aligned with respect to diaphragm 170. In further alternative embodiments, pin 186 is not inserted through diaphragm 170. In yet other alternative embodiments, face 187 includes a ventilation component, such as a surface imperfection or indentation, to promote an intentional leak and/or venting to facilitate preventing long term pressure differential buildup inside chamber 110 as compared to ambient conditions. In further alternative embodiments, diaphragm 170 is over-molded onto a hard face element to create a single part that is then assembled to an armature 189. In such embodiments, pin 186 is not required to be an air-tight seal in diaphragm penetration 171, but rather, diaphragm 170 seals primarily where hub undercut 280 surrounds armature end 200.

Diaphragm 170 is moved to enable a breath sample to enter into fuel cell housing assembly 102, and is reset by actuator 184, as described herein. Actuator 184 is operable between hard stops. In one embodiment, actuator 184 is a low-power latching electrical solenoid. It should be noted that actuator 184 is not limited to being a low-power latching electrical solenoid, and rather any other actuator, or actuating device, could be utilized that enables fuel cell housing assembly 102 and sampling system 100 to function as described herein. Thus, diaphragm 170 is movable between a repeatable start position (reset), shown in FIG. 8, and a repeatable end position (sample), shown in FIG. 7.

Generally, when system 100 is not in use, diaphragm 170 is in the reset position. In the reset position, diaphragm 170 is in its "as-molded" shape such that no internal stresses are induced to diaphragm 170. Moreover, when diaphragm 170 is in the reset position, diaphragm 170 is positioned in sealing contact against inlet tube end 126, such that inlet tube 122 is completely sealed from cavity 110. In alternative embodiments, inlet tube end 126 includes a ventilation component, such as an indentation or imperfection, which facilitates promoting an intentional leak and/or venting to prevent long term pressure differential buildup between cavity 110 and ambient conditions in inlet tube 122. In the sample position, diaphragm 170 is moved a repeatable distance $d_3$ from inlet tube end 126 such that inlet tube 122 is open and unobstructed to allow a breath sample to enter housing assembly 102.

During assembly, when housing components 106 and 108 are pressed together, diaphragm 170, clamp ring 240, fuel cell 104, backup disk 111, and fuel cell wires 250 are tightly coupled in position. As shown in FIG. 4, although components 106, 108, 170, 240, 104, and 111 each have a generally circular cross-sectional shape, it should be noted that such components can have different shapes in different embodiments. The two rigid fuel cell housing components 106 and 108 are press-fit together such that diaphragm 170 is retained in position by coupling ring offset 274. Specifically, when housing assembly 102 is assembled, clamp ring 240 is positioned between fuel cell 104 and diaphragm 170, and diaphragm rim 176 is tightly received within housing coupling portion area 276. As such, when housing assembly 102 is fully assembled, portions 106 and 108 provide an air-tight sealed assembly around the periphery of diaphragm 170 using no fasteners or glue. Moreover, when housing assembly 102 is assembled, it applies pressure to "sandwich" components 170, 240, 104, 111, and wires 250 together such that sealing and electrical contact is facilitated within housing assembly 102. Diaphragm rim 176 provides a flexible element in the "sandwich" to accommodate any tolerances in the assembly. The fuel cell wires 250 (which contact fuel cell 104 itself) exit out of fuel cell housing assembly 102 through small holes 262 that are sealed by epoxy. In the exemplary embodiment, clamp ring 240 includes a chamfer 290 that facilitates ensuring clearance for fuel cell wires 250 exiting fuel cell housing assembly 102.

Furthermore, fuel cell housing assembly 102 can be easily opened and re-closed to replace a fuel cell 104 without the use of fasteners, glue, or heat seal. Moreover, because fuel cell housing assembly 102 only includes eight parts (including two fuel cell wires 250, fuel cell 104, backup disk 111, diaphragm 170, and three molded parts 106, 108, and 240), assembly 102 is easily assembled prior to being attached to a non-integral actuator 184. Such a construction facilitates reducing mechanical wear within fuel cell housing assembly 102 during operation of sampling system 100, and facilitates the use of a solenoid actuator 184 that operates with little or no mechanical wear.

Alternative embodiments use solvent or glue to provide additional adhesion between housing components 106 and 108, in addition to the press-fit. In one embodiment, the adhesive is a break-away type of adhesive. Moreover, in other embodiments, a slot may be formed at the outside seam where housing components 106 and 108 are coupled together, to facilitate the components being easily separated when the components are glued or press-fit together. In another alternative embodiment, housing components 106 and 108 are slip-fit together and then bonded together with glue.

Whether housing components 106 and 108 are press-fit, slip-fit, or otherwise aligned and joined, a molded latching element, such as an undercut, may be used to facilitate retention of components. Within such an embodiment, the latching element could be molded integrally together, or coupled to housing components 106 and 108. Moreover, the latching element could be located on the outside surfaces of either component, or elsewhere in the assembly, such as within housing components 106 and 108. In a further alternative embodiment, housing components 106 and 108 are removably coupled when assembly 102 is inserted within a clamp or a case, as part of being integrated into a breath test instrument or other such instrument for sampling and measuring alcohol.

During breath testing, when actuator 184 is powered to take a sample, armature 189 moves away from breath inlet tube end 126 quickly, pulling diaphragm 170 at its hub 178 off of inlet tube 122. As diaphragm 170 is moved further away from breath inlet tube 122, it begins drawing a measured sample of breath into fuel cell housing assembly 102. More specifically, actuator 184 moves until it reaches a hard stop against magnet 278. Power is removed from actuator 184 and the assembly remains in the sample position due to magnet 278. In the exemplary embodiment, a spacer 214 formed by head of pin 216 facilitates reducing an amount of magnetic power used to retain armature 189 against spacer 214. Alternatively, housing assembly 102 does not include spacer 214.

As the breath sample enters the fuel cell housing assembly 102, the breath sample flows through the center of fuel cell 104, and is discharged into cavity 110 but starting at a point slightly above the surface of fuel cell 104. As such, the breath sample is distributed substantially evenly in a polar fashion 360° and across the round fuel cell 104. The breath sample is also distributed radially from the center of the fuel cell 104 towards its outer periphery. Thus, any alcohol molecules in the breath sample have a substantially nearly equal opportunity to start the reaction with fuel cell 104 at approximately the same time. Moreover, the orientation of the inlet tube 122 to the fuel cell 104 also facilitates distributing the work of the reaction across the entire face of the fuel cell 104. Electrons produced by the reaction are drained off as quickly as possible by the external circuit, and the resulting voltage curves are integrated as quickly as possible to produce a quick and accurate result for the operator performing the breath test.

Once the reading has been obtained, actuator 184 is powered with reverse polarity compared to the polarity used during the breath sample mode, and as a result, the actuator armature 189 is quickly moved away from magnet 278 towards the breath inlet tube 122. The breath sample is therefore expelled out the breath inlet tube 122, until the actuator 184 reaches a hard stop wherein the diaphragm hub 178 is positioned against the breath inlet tube end 126. When the diaphragm 170 is in this position, the fuel cell housing assembly 102 is again sealed off from the environment, with the exception of a very small imperfection formed in the seal to facilitate pressure equalization between assembly 102 and ambient pressure during changing ambient pressure conditions.

Power is then removed from actuator 184 and spring 218 biases the actuator 184, and sample system 100 in this reset position. A chamfered cylindrical surface 286 formed within coupling portion 108 facilitates maintaining the large diameter end 230 of tapered spring 218 centered with respect to armature 189 such that the spring force induced therefrom is always exerted generally axially. In an alternative embodiment, washer 222 is shaped to substantially conform to a shape of diaphragm 170, as defined by, an outside shape of hub 178 such that diaphragm 170 is substantially prevented from dislodging from armature 189. In another alternative embodiment, housing assembly 102 is sealed from ambient and the environment when the diaphragm hub 178 is positioned against breath inlet tube end 126. When in the reset position, the diaphragm 170 is in its natural, as-molded position against the inlet tube 122, such that no significant stresses are induced within the diaphragm 170 itself.

During sampling, the diaphragm 170 moves to a position which minors the reset position, as the diaphragm 170 bends at its periphery next to its outermost edge at which the diaphragm 170 is clamped for an air-tight seal. The diaphragm 170 moves smoothly, without buckling or folding on itself when moving from the reset position to the sample position. The inlet tube 122 need not be so small as to be subjected to freezing-up, or as to significantly slow down the sampling process, yet is small enough to be easily sealed by the diaphragm 170 with small forces. In alternative embodiments, diaphragm 170 is designed to fold on itself or is otherwise designed to allow for non-axial movement of the portion of diaphragm 170 extending between hub 178 and its periphery. Accordingly, the minimum amount of force required for axial movement is facilitated to be reduced. In one embodiment, when actuator 184 is moved from the sample position to the reset position, or vice versa, an electronic signal is generated that verifies the operation of the actuator.

In an alternative embodiment, sampling system 100 does not include magnet 278, or any other magnetic device. Specially, in such an embodiment, actuator 184 is not magnetically coupled to any component when the assembly is in the sample position. Rather, during breath testing, when actuator 184 is powered to take a sample, armature 189 moves away from breath inlet tube end 126 quickly, until the actuator 184 reaches a hard stop, such that diaphragm 170 is pulled at its hub 178 off of inlet tube 122. As diaphragm 170 is moved further away from breath inlet tube 122, a measured sample of breath is drawn into fuel cell housing assembly 102.

When power is removed from actuator 184, the assembly is immediately reset such that chamber 110 is again sealed from ambient and the environment. More specifically, in the exemplary embodiment, when power is removed, actuator 184 is moved via spring 218 until it reaches the hard stop in the reset position such that diaphragm hub 178 is positioned against breath inlet tube end 126 without being powered with reverse polarity. The breath sample, or more specifically, the portion of the breath sample absorbed in fuel cell 104, is then analyzed, as described herein. More specifically, in such an embodiment, the system is in the reset position during the entire analysis of the breath sample. As a result, the elapsed time between sampling and resetting is reduced such that the possibility of gas diffusion within chamber 110, i.e., gases diffusing into chamber 110 during analysis, is facilitated to be reduced regardless of the time necessary to complete the analysis of the breath sample. Moreover, in such an embodiment, the volume of the breath sample drawn into system 100 remains constant from sample to sample.

In such an embodiment, when actuator 184 is moved from the sample position to the reset position, or vice versa, a signal, such as an electrical signal or a mechanical signal, may be generated by the sampling assembly that verifies the operation of the actuator. In such an embodiment, the signal generated by the sampling assembly may, provide a visual indication, or may be sensed by a component external to the sampling assembly, such as, but not limited to, a sensor, or receiving circuitry. Furthermore, in some embodiments, the electronic signal could be generated external to the sampling assembly and transmitted into the sampling assembly to verify the physical condition of the assembly at that time, or across a predetermined time period. For example, the physical condition of the sampling assembly could be verified by measuring the inductance or the changing inductance of the device by applying a known electronic signal of a specified voltage and frequency, and then measuring how that signal is impacted, effected, or altered by the physical condition of the sampling assembly.

In another alternative embodiment, the assembly includes a timing mechanism, such as, but not limited to, a processor, mechanical hardware, and/or electrical hardware such as a latching mechanism and/or a delay circuit, that provides a time delay for movement of the actuator from the sample position to the reset position. Specifically, in such an alternative embodiment, as power is removed from actuator 184, the timing mechanism ensures that the actuator remains or "dwells" in the sample position for a pre-selected amount of time prior to moving to the reset position. In such an embodiment, when actuator 184 is moved from the sample position to the reset position, or vice versa, an electronic signal may be generated that verifies the operation of the actuator.

The above-described sampling assembly and fuel cell assembly facilitate performing alcohol testing that is accurate, reliable, inexpensive, long-lasting, and quick, using small amounts of energy in the process. The combination of fuel cell and actuator also facilitates quick cycle times between tests, and has many advantages contributing to long term calibration stability. In addition, the fuel cell housing assembly is of a small enough size and mass to be practical in a handheld unit to allow traditional resistance heating (or thermoelectric heating and cooling) using very low amounts of energy with quick warm-up times.

Various alternative embodiments to the embodiments illustrated in FIGS. 4-8 are possible and contemplated. For example, rather than being mounted to the fuel cell assembly, the actuator could be mounted to a printed circuit board or to an instrument case. Furthermore, the end of the breath inlet tube inside the fuel cell could be in one of many different various selected shapes to facilitate improved distribution of the sample evenly across the fuel cell surface. Also, the end of the breath inlet tube inside the fuel cell could have a designed imperfection on the rim so as not to seal off the fuel cell completely from outside air. Moreover, a variety of actuators could be used to exercise the fuel cell diaphragm for sample and reset. For example, right angle actuators or actuators with mechanical advantage could be used.

Exemplary embodiments of fuel cell housing assemblies and sampling assemblies are described above in detail. None of the assemblies or components are limited to the specific embodiments described herein, but rather, components of each assembly may be utilized independently and separately from other components described herein. For example, although the sampling system has been described in the context of using the integration method, it is contemplated that the assembly could also be used with peak measurement method and other alternative methods. Moreover, although many of the components are described and illustrated having a generally circular and planar shape, the components could be formed with a non-circular shape and/or non-planar shape. In addition, each component need not have the same planar shape.

It is further contemplated that the fuel cell housing may need to be unsealed momentarily at the inlet and then re-sealed before a breath sample is taken to equalize any pressure difference that may have developed between the inside and outside of the fuel cell housing due to ambient pressure changes, such as due to weather or elevation changes, or temperature changes since the fuel cell housing was last sealed after a sample. In a sense, a faux sample could be taken by the assembly by taking a sample and resetting very quickly, for example, during the initial power-on of the instrument before it is ready for the person being tested to blow. Such a "burping" operation facilitates substantially equalizing pressure conditions outside and inside the sampler before the person being tested blows and an alcohol sample is taken from the breath for analysis. There would be no measurement during this faux sample. Alternatively, this "burping" could be accomplished by taking a "blank" measurement cycle to test for alcohol in the mouthpiece before blowing as part of a standard pre-test before the human test. A mouthpiece "blank" measurement does not require a precision measurement so it could serve two purposes: proving that nominally there is no alcohol in mouthpiece and "burping" the assembly. Either of these methods could contribute to always getting a consistent sample on the human breath. This approach would not require the intentional small leak at the inlet as described herein. Also, the fuel cell wires could exit the fuel cell housing through the diaphragm which when clamped, would provide an air-tight seal around the wires without epoxy.

Further, the sampling system/fuel cell assembly could be cycled more than once or repeatedly in the course of a taking a "single" sample. Such cycling may facilitate sampling ambient air in a passive testing mode or for other reasons.

Also, the backup disk containing extra electrolyte could be omitted between the fuel cell and the housing wall. Further, the outer edge of the diaphragm could be shaped to allow more flexibility in taking up any tolerances such as a v-shape or half-round shape in cross-section. As an alternative to the clamp, an O-ring could be used between the diaphragm and the fuel cell. In yet another alternative, the clamping ring could be eliminated. Additionally, the fuel cell housing could be held together by any fastening mechanism which enables the fuel cell housing to function as described herein, such as but not limited to the use of fasteners, or glue instead of a press-fit, or with the use of heat or ultrasonic sealing.

While the invention has been described in terms of various specific embodiments, those skilled in the art will recognize that the invention can be practiced with modification within the spirit and scope of the claims.

What is claimed is:

1. A fuel cell assembly, said assembly comprising
a fuel cell;
a fuel cell housing comprising an endwall and an inlet port extending through said endwall, said inlet port for admitting a breath sample into said housing; and
a diaphragm coupled within said housing such that a cavity is defined between said housing and said diaphragm, said fuel cell positioned within said cavity and substantially concentrically aligned with respect to said inlet port.

2. A fuel cell assembly in accordance with claim 1 wherein said fuel cell comprises a first side, a second side, and an opening extending therebetween.

3. A fuel cell assembly in accordance with claim 1 wherein said inlet port extends a distance radially from said housing endwall, said fuel cell comprises an opening extending therethrough and sized to receive at least a portion of said inlet port therethrough.

4. A fuel cell assembly in accordance with claim 1 wherein said diaphragm is selectively movable between a sampling position and a reset position.

5. A fuel cell assembly in accordance with claim 4 wherein said diaphragm is molded and remains in its natural as-molded state when in the reset position.

6. A fuel cell assembly in accordance with claim 1 wherein said diaphragm is flexible and comprises a first side and a second side, each of said first and second sides are bordered by an outer edge, at least one of said first side and said second side comprises at least a portion of a hub for coupling said diaphragm to an actuator.

7. A fuel cell assembly in accordance with claim 6 wherein said diaphragm first side extends substantially continuously across said diaphragm.

8. A fuel cell assembly in accordance with claim 6 wherein one of said diaphragm first and second sides comprises a rim extending outwardly from said diaphragm side, said rim for coupling said diaphragm within said housing.

9. A fuel cell assembly in accordance with claim 1 further comprising a substantially cylindrical body extending between said diaphragm and said fuel cell.

10. A fuel cell assembly in accordance with claim 9 wherein said body comprises a clamping mechanism that facilitates securing at least one of said fuel cell and said diaphragm within said housing.

11. A fuel cell assembly in accordance with claim 1 wherein said housing further comprises a sidewall extending from said endwall, said diaphragm coupled in sealing contact against said housing sidewall.

12. A fuel cell assembly in accordance with claim 11 wherein said diaphragm is moveable between a first position and a second position without buckling.

13. A fuel cell assembly in accordance with claim 11 wherein said diaphragm is moveable from a first position and a second position without being folded.

14. A fuel cell assembly in accordance with claim 11 wherein said diaphragm remains in sealing contact with said housing sidewall when moved between the first and second positions.

15. A fuel cell assembly in accordance with claim 1 wherein said diaphragm is selectively movable to seal said inlet port to prevent airflow through said inlet port into said housing cavity.

16. A fuel cell assembly in accordance with claim 1 wherein said diaphragm is selectively movable to substantially seal said inlet port.

17. A fuel cell assembly in accordance with claim 1 wherein said inlet port is formed integrally with said housing endwall.

18. A fuel cell assembly in accordance with claim 1 wherein said housing further comprises a first housing portion and a second housing portion removably coupled to said first housing portion, only said first housing portion comprises said end wall.

19. A fuel cell assembly in accordance with claim 18 wherein said diaphragm is only coupled within said first housing portion.

20. A fuel cell assembly in accordance with claim 18 wherein said first housing portion is removably coupled to said second housing portion in a press fit coupling arrangement.

21. A fuel cell assembly in accordance with claim 18 wherein at least one of said first housing portion and said second housing portion further comprises an undercut configured to facilitate coupling said first and second housing portions together.

22. A fuel cell assembly in accordance with claim 18 wherein said housing assembly is used in a handheld breath tester.

23. A fuel cell assembly in accordance with claim 1 wherein said inlet port is configured to distribute a breath sample substantially evenly across said fuel cell.

24. A fuel cell assembly in accordance with claim 1 wherein said fuel cell is substantially planar.

25. An assembly comprising:
a fuel cell housing having a centerline extending therethrough, said housing comprising an inlet port extending through and concentrically aligned with respect to said housing;
a fuel cell positioned within said housing such that said fuel cell is substantially concentrically aligned with respect to said housing, said fuel cell comprising an opening extending therethrough and concentrically aligned with respect to said inlet port for admitting a breath sample into said housing; and
an actuator removably coupled to said housing.

26. An assembly in accordance with claim 25 wherein said housing assembly is used in a handheld breath tester.

27. An assembly in accordance with claim 25 wherein said housing further comprises a first housing portion and a second housing portion removably coupled to said first housing portion, said first housing portion comprises an end wall and a sidewall circumscribing said endwall and extending therefrom.

28. An assembly in accordance with claim 27 wherein said first housing portion is removably coupled to said second housing portion in a press fit coupling arrangement.

29. An assembly in accordance with claim 27 wherein at least one of said first housing portion and said second housing portion further comprises an undercut configured to facilitate coupling said first and second housing portions together.

30. An assembly in accordance with claim 25 further comprising an inlet port extending through said housing, said inlet port concentrically aligned with respect to said housing, at least a portion of said inlet port extends through said fuel cell opening.

31. An assembly in accordance with claim 30 wherein said inlet port is configured to distribute a breath sample substantially evenly across said fuel cell.

32. An assembly in accordance with claim 30 wherein said inlet port extends a radial distance from an outer surface of said fuel cell.

33. An assembly in accordance with claim 30 wherein said inlet port is formed integrally with said housing.

34. An assembly in accordance with claim 25 further comprising a diaphragm coupled within said housing such that a cavity is defined between said housing and said diaphragm, said fuel cell positioned within said cavity.

35. An assembly in accordance with claim 34 wherein said diaphragm is selectively movable between a sampling position and a reset position.

36. An assembly in accordance with claim 35 wherein said diaphragm is molded and remains in its natural as-molded state when in the reset position.

37. An assembly in accordance with claim 34 wherein said diaphragm is flexible and comprises a first side and a second side, each of said first and second sides are bordered by an outer edge, at least one of said first side and said second side comprises at least a portion of a hub for coupling said diaphragm to an actuator.

38. An assembly in accordance with claim 37 wherein said diaphragm first side extends continuously across said diaphragm.

39. An assembly in accordance with claim 37 wherein one of said diaphragm first and second sides comprises a rim extending outwardly from said diaphragm side, said rim for coupling said diaphragm within said housing.

40. An assembly in accordance with claim 34 further comprising a substantially cylindrical body extending between said diaphragm and said fuel cell.

41. An assembly in accordance with claim 40 wherein said body facilitates securing at least one of said fuel cell and said diaphragm within said housing.

42. An assembly in accordance with claim 34 wherein said housing further comprises a sidewall extending from an endwall, said diaphragm coupled in sealing contact against said housing sidewall such that said cavity is defined between said diaphragm and said end wall.

43. An assembly in accordance with claim 34 wherein said diaphragm is coupled to said actuator and is selectively moveable within said housing without buckling.

44. An assembly in accordance with claim 34 wherein said diaphragm is coupled to said actuator and is selectively moveable within said housing without being folded.

45. An assembly in accordance with claim 34 wherein said diaphragm remains in sealing contact with said housing when moved by said actuator.

46. An assembly in accordance with claim 34 wherein said diaphragm is selectively movable to prevent airflow into said housing cavity.

47. An assembly in accordance with claim 34 wherein said diaphragm is selectively movable to substantially seal said housing cavity from the environment external to said housing.

48. A fuel cell housing assembly comprising:
a fuel cell housing defining a cavity therein; and
a fuel cell comprising an outer surface, an inner surface, and an opening extending therebetween, said opening substantially concentrically aligned with respect to an inlet port for permitting a breath sample to be drawn into said cavity and dispersed substantially evenly across said fuel cell.

49. An assembly in accordance with claim 48 wherein said housing assembly is used in a handheld breath tester.

50. An assembly in accordance with claim 48 wherein said housing comprises an endwall and a sidewall circumscribing said endwall and extending radially therefrom, said endwall comprises an inlet port extending therethrough and substantially concentrically aligned with respect to said housing endwall, at least a portion of said inlet port extends through said fuel cell opening such that a tip of said inlet port remains a distance from said fuel cell outer surface.

51. An assembly in accordance with claim 50 wherein said housing comprises a plurality of body portions removably coupled together in a press fit coupling arrangement.

52. An assembly in accordance with claim 51 wherein at least one of said plurality of body portions comprises an undercut configured to facilitate coupling said plurality of body portions together.

53. An assembly in accordance with claim 51 wherein said inlet port is formed integrally with one of said housing plurality of body portions.

54. An assembly in accordance with claim 50 further comprising a diaphragm removably coupled within said housing such that said diaphragm outer periphery is in sealing contact with said housing, said diaphragm defining a portion of said cavity.

55. An assembly in accordance with claim 54 wherein said diaphragm is selectively movable between a sampling position and a reset position.

56. An assembly in accordance with claim 54 wherein said diaphragm comprises a first side and an opposite second side, one of said first side and said second side extends continuously across said diaphragm, at least one of said diaphragm first and second sides comprises at least a portion of a hub that is substantially concentrically aligned with respect to said diaphragm.

57. An assembly in accordance with claim 54 further comprising a substantially cylindrical body extending between said diaphragm and said fuel cell, said cylindrical body facilitates securing said diaphragm and said fuel cell within said housing.

58. An assembly in accordance with claim 54 further comprising an actuator removably coupled to said housing, said actuator configured to selectively move said diaphragm towards and away from said inlet port without folding said diaphragm.

59. An assembly in accordance with claim 58 wherein said diaphragm outer periphery remains in sealing contact with said housing during operation of said actuator.

60. An assembly in accordance with claim 54 wherein said diaphragm is selectively movable to substantially seal said inlet port.

61. A fuel cell housing assembly for use with a breath tester, said housing assembly comprising:
a fuel cell;
a fuel cell housing comprising an endwall and an inlet port extending through said endwall, said inlet port for admitting a breath sample into said housing; and
a diaphragm coupled within said housing such that a cavity is defined between said housing and said diaphragm, said fuel cell positioned within said cavity and substantially concentrically aligned with respect to said inlet port, said diaphragm is selectively movable between a sampling position when a breath sample is admitted into said housing and a reset position wherein airflow into said housing is substantially prevented.

62. An assembly in accordance with claim 61 wherein said diaphragm is coupled to an actuator, said actuator is coupled to a power source to selectively control movement of said diaphragm between the sampling position and the reset position.

63. An assembly in accordance with claim 62 wherein energization of said actuator causes said diaphragm to move from the reset position to the sampling position, and wherein deenergization of said actuator causes said diaphragm to move from the sampling position to the reset position.

64. An assembly in accordance with claim 63 further comprising a timing mechanism configured to delay movement for a preselected amount of time of said actuator from the sampling position to the reset position.

65. An assembly in accordance with claim 61 further comprising a magnet configured to retain said diaphragm in the sampling position.

66. A fuel cell assembly in accordance with claim 61 wherein said diaphragm is molded and remains in its natural as-molded state when in the reset position.

67. A fuel cell assembly in accordance with claim 61 said diaphragm is moveable between the sample position and the reset position without buckling.

68. A fuel cell assembly in accordance with claim 61 wherein said diaphragm is moveable between the sample position and the reset position without being folded.

69. A fuel cell assembly in accordance with claim 61 wherein said diaphragm substantially seals said inlet port to prevent airflow through said inlet port into said housing cavity when in the reset position.

70. A fuel cell assembly in accordance with claim 61 wherein said inlet port is configured to distribute a breath sample substantially evenly across said fuel cell.

* * * * *